(12) United States Patent
Miyamoto et al.

(10) Patent No.: US 7,873,483 B2
(45) Date of Patent: Jan. 18, 2011

(54) ANALYZER AND COMPUTER PROGRAM PRODUCT

(75) Inventors: Kimiyo Miyamoto, Kakogawa (JP); Tashiro Osumi, Kyoto (JP)

(73) Assignee: Sysmex Corporation, Hyogo (JP)

( * ) Notice: Subject to any disclaimer, the term of this patent is extended or adjusted under 35 U.S.C. 154(b) by 0 days.

(21) Appl. No.: 11/168,408

(22) Filed: Jun. 29, 2005

(65) Prior Publication Data

US 2006/0004530 A1 Jan. 5, 2006

(30) Foreign Application Priority Data

Jul. 2, 2004 (JP) .............................. 2004-197184

(51) Int. Cl.
*G01N 31/00* (2006.01)

(52) U.S. Cl. .............................. 702/30; 702/31; 422/50

(58) Field of Classification Search .............. 702/21–32
See application file for complete search history.

(56) References Cited

U.S. PATENT DOCUMENTS

| 5,728,351 | A | 3/1998 | Carver, Jr. | |
| 6,268,217 | B1* | 7/2001 | Barton et al. | 436/66 |
| 6,391,263 | B1* | 5/2002 | Mishima et al. | 422/67 |
| 6,537,213 | B2* | 3/2003 | Dodds | 600/300 |
| 2003/0064757 | A1* | 4/2003 | Yamadera et al. | 455/566 |
| 2003/0235920 | A1* | 12/2003 | Wyatt et al. | 436/63 |
| 2006/0100788 | A1* | 5/2006 | Carrino et al. | 702/19 |

FOREIGN PATENT DOCUMENTS

| JP | 2000310642 A | 11/2000 |
| JP | 2001-013130 A | 1/2001 |
| WO | 02068963 A1 | 9/2002 |

\* cited by examiner

*Primary Examiner*—Manuel L Barbee
(74) *Attorney, Agent, or Firm*—Sughrue Mion, PLLC

(57) ABSTRACT

Provided is an analyzer capable of analyzing an analyte with an analytical condition corresponding to a minor classification prepared by subdividing the species (major classification) of the analyte. This analyzer selects a major classification corresponding to the analyte to be analyzed from a plurality of major classifications indicating the types of analytes, preferentially displays minor classifications, belonging to the selected major classification, prepared by subdividing the corresponding major classification, selects one of the displayed minor classifications, and analyzes the analyte on the basis of an analytical condition corresponding to the selected minor classification.

11 Claims, 12 Drawing Sheets

FIG.4

MEASUREMENT REGISTRATION SCREEN

| SAMPLE NUMBER | CATEGORY | ANIMAL SPECIES | DISCRETE | RACK | TEST TUBE POSITION | STATUS | SAMPLE COMMENT |
|---|---|---|---|---|---|---|---|
| 103 | RAT STANDARD | RAT | CBC+DIFF+RET | 1 | 5 | COMP | rat CBC+DIFF+RET |
| 104 | | RAT | CBC+DIFF+RET | 0 | 1 | PEND | |
| 105 | | RAT | CBC+DIFF+RET | 0 | 2 | PEND | |
| 106 | | RAT | CBC+DIFF+RET | 0 | 3 | ERR | |
| 107 | | RAT | CBC+DIFF+RET | 0 | 4 | PEND | |
| 108 | | RAT | CBC+DIFF+RET | 0 | 5 | PEND | |
| 109 | | RAT | CBC+DIFF+RET | 0 | 6 | PEND | |
| 110 | | RAT | CBC+DIFF+RET | 0 | 7 | PEND | |
| 111 | | RAT | CBC+DIFF+RET | 0 | 8 | PEND | |
| 112 | | RAT | CBC+DIFF+RET | 0 | 9 | PEND | |
| 113 | | RAT | CBC+DIFF+RET | 0 | 10 | PEND | |
| 114 | | RAT | CBC+DIFF+RET | 1 | 1 | PEND | |
| 115 | | RAT | CBC+DIFF+RET | 1 | 2 | COMP | |
| 116 | | RAT | CBC+DIFF+RET | 1 | 3 | ERR | |
| 117 | | RAT | CBC+DIFF+RET | 1 | 4 | PEND | |

SAMPLE NUMBER 103
RACK 1
TEST TUBE POSITION 5
ANIMAL SPECIES: RAT
CATEGORY: RAT STANDARD
DISCRETE: CBC+DIFF+RET
SAMPLE COMMENT: rat CBC+DIFF+RET CATEGORY INFORMATION
CATEGORY NAME: RAT STANDARD
ANIMAL SPECIES: RAT    SEXUALITY: EITHER SEX
AGE UNIT: MONTH    LOWER AGE LIMIT: 0.0    UPPER AGE LIMIT: 999.0

FIG.5 MEASUREMENT REGISTRATION SCREEN

| SAMPLE NUMBER | CATEGORY | ANIMAL SPECIES | DISCRETE | RACK | TEST TUBE POSITION | STATUS | SAMPLE COMMENT |
|---|---|---|---|---|---|---|---|
| 103 | RAT STANDARD | RAT | CBC+DIFF+RET | 1 | 5 | COMP | rat CBC+DIFF+RET |
| 104 | | RAT | CBC+DIFF+RET | 0 | 1 | PEND | |
| 105 | | RAT | CBC+DIFF+RET | 0 | 2 | PEND | |
| 106 | | RAT | CBC+DIFF+RET | 0 | 3 | ERR | |
| 107 | | RAT | CBC+DIFF+RET | 0 | 4 | PEND | |
| 108 | | RAT | CBC+DIFF+RET | 0 | 5 | PEND | |
| 109 | | RAT | CBC+DIFF+RET | 0 | 6 | PEND | |
| 110 | | RAT | CBC+DIFF+RET | 0 | 7 | PEND | |
| 111 | | RAT | CBC+DIFF+RET | 0 | 8 | PEND | |
| 112 | | RAT | CBC+DIFF+RET | 0 | 9 | PEND | |
| 113 | | RAT | CBC+DIFF+RET | 0 | 10 | PEND | |
| 114 | | RAT | CBC+DIFF+RET | 1 | 1 | PEND | |
| 115 | | RAT | CBC+DIFF+RET | 1 | 2 | COMP | |
| 116 | | RAT | CBC+DIFF+RET | 1 | 3 | ERR | |
| 117 | | RAT | CBC+DIFF+RET | 1 | 4 | PEND | |

SAMPLE NUMBER 103
ANIMAL SPECIES
CATEGORY RACK 1 TEST TUBE POSITION 5
DISCRETE
SAMPLE COMMENT
CATEGORY INF

RAT
MOUSE
RABBIT
DOG
MONKEY
Other

ANIMAL SPECIES:
CATEGORY
AGE UNIT:
SEXUALITY:
LOWER AGE LIMIT:
UPPER AGE LIMIT:

FIG.6 MEASUREMENT REGISTRATION SCREEN

| SAMPLE NUMBER | CATEGORY | ANIMAL SPECIES | DISCRETE | RACK | TEST TUBE POSITION | STATUS | SAMPLE COMMENT |
|---|---|---|---|---|---|---|---|
| 103 | RAT STANDARD | RAT | CBC+DIFF+RET | 1 | 5 | COMP | rat CBC+DIFF+RET |
| 104 | | RAT | CBC+DIFF+RET | 0 | 1 | PEND | |
| 105 | | RAT | CBC+DIFF+RET | 0 | 2 | PEND | |
| 106 | | RAT | CBC+DIFF+RET | 0 | 3 | ERR | |
| 107 | | RAT | CBC+DIFF+RET | 0 | 4 | PEND | |
| 108 | | RAT | CBC+DIFF+RET | 0 | 5 | PEND | |
| 109 | | RAT | CBC+DIFF+RET | 0 | 6 | PEND | |
| 110 | | RAT | CBC+DIFF+RET | 0 | 7 | PEND | |
| 111 | | RAT | CBC+DIFF+RET | 0 | 8 | PEND | |
| 112 | | RAT | CBC+DIFF+RET | 0 | 9 | PEND | |
| 113 | | RAT | CBC+DIFF+RET | 0 | 10 | PEND | |
| 114 | | RAT | CBC+DIFF+RET | 1 | 1 | COMP | |
| 115 | | RAT | CBC+DIFF+RET | 1 | 2 | COMP | |
| 116 | | RAT | CBC+DIFF+RET | 1 | 3 | ERR | |
| 117 | | RAT | CBC+DIFF+RET | 1 | 4 | PEND | |

SAMPLE NUMBER: 103
ANIMAL SPECIES: RAT
CATEGORY: RAT STANDARD
DISCRETE:
SAMPLE COMMENT:
CATEGORY INFORMATION
  ANIMAL SPECIES:
  AGE UNIT:
  SEXUALITY:
  LOWER AGE LIMIT:
  UPPER AGE LIMIT:
RACK: 1
TEST TUBE POSITION: 5

Options: RAT001, RAT002, RAT003, RAT004

FIG.7
CATEGORY REGISTRATION SCREEN

| | | CATEGORY NAME | ANIMAL SPECIES | LOWER AGE LIMIT | UPPER AGE LIMIT | AGE UNIT | SEXUALITY |
|---|---|---|---|---|---|---|---|
| 1 | ☒ | RAT STANDARD | RAT | 0.0 | 999.0 | MONTH | EITHER SEX |
| 2 | ☒ | MOUSE STANDARD | MOUSE | 0.0 | 30.0 | WEEK | EITHER SEX |
| 3 | ☒ | MONKEY STANDARD | MONKEY | 0.0 | 30.0 | YEAR | EITHER SEX |
| 4 | ☒ | Other | MONKEY | 0.0 | 100.0 | YEAR | EITHER SEX |
| 5 | ☐ | a | | 0.0 | 0.0 | YEAR | EITHER SEX |
| 6 | ☐ | b | | 0.0 | 0.0 | YEAR | EITHER SEX |
| 7 | ☐ | c | | 0.0 | 0.0 | YEAR | EITHER SEX |
| 8 | ☐ | d | | 0.0 | 0.0 | YEAR | EITHER SEX |
| 9 | ☐ | e | | 0.0 | 0.0 | YEAR | EITHER SEX |
| 10 | ☐ | f | | 0.0 | 0.0 | YEAR | EITHER SEX |
| 11 | ☐ | g | | 0.0 | 0.0 | YEAR | EITHER SEX |
| 12 | ☐ | h | | 0.0 | 0.0 | YEAR | EITHER SEX |
| 13 | ☐ | i | | 0.0 | 0.0 | YEAR | EITHER SEX |
| 14 | ☐ | j | | 0.0 | 0.0 | YEAR | EITHER SEX |
| 15 | ☐ | k | | 0.0 | 0.0 | YEAR | EITHER SEX |
| 16 | ☐ | l | | 0.0 | 0.0 | YEAR | EITHER SEX |
| 17 | ☐ | aaaa | MONKEY | 0.0 | 0.0 | YEAR | EITHER SEX |
| 18 | ☒ | Mouse-001 | MOUSE | 0.0 | 0.0 | YEAR | EITHER SEX |
| 19 | ☒ | Mouse-002 | MOUSE | 0.0 | 0.0 | YEAR | EITHER SEX |
| 20 | ☒ | Mouse-003 | MOUSE | 0.0 | 0.0 | YEAR | EITHER SEX |
| 21 | ☐ | | | | | | |
| 22 | ☐ | | | | | | |
| 23 | ☐ | | | | | | |
| 24 | ☐ | | | | | | |

CATEGORY REGISTRATION
CATEGORY: RAT STANDARD
ANIMAL SPECIES: RAT
UPPER AGE LIMIT: 999
LOWER AGE LIMIT: 0
AGE UNIT: MONTH
SEXUALITY: EITHER SEX
COMMENT:

FIG.8

FLAGGING DETERMINATION VALUE SET SCREEN

CATEGORY: RAT STANDARD  ANIMAL SPECIES: RAT  AGE UNIT: YEAR  SEXUALITY: EITHER SEX

LOWER AGE LIMIT: 0.0  UPPER AGE LIMIT: 999.9

| WBC | RBC/RET | PLT | EXTENDED DIFF | EXTENDED W/B | EXTENDED RET |

WBC ABNORMAL FLAG

| ☑ Neutropenia: | NEUT# | < | 10.0 | 10^2/μL | or | NEUT% | < | 10.0 | % |
| ☑ Neutrophilia: | NEUT# | > | 32.0 | 10^2/μL | or | NEUT% | > | 99.9 | % |
| ☑ Lymphopenia: | LYMPH# | < | 0.0 | 10^2/μL | or | LYMPH% | < | 0.0 | % |
| ☑ Lymphocytosis: | LYMPH# | > | 40.0 | 10^2/μL | or | LYMPH% | > | 50.0 | % |
| ☑ Monocytosis: | MONO# | > | 8.0 | 10^2/μL | or | MONO% | > | 99.9 | % |
| ☑ Eosinophilia: | EO# | > | 3.0 | 10^2/μL | or | EO% | > | 99.9 | % |
| ☑ Basophilia: | BASO# | > | 1.0 | 10^2/μL | or | BASO% | > | 99.9 | % |
| ☑ Leukocytopenia: | WBC# | < | 10.0 | 10^2/μL | | | | | |
| ☑ Leukocytosis: | WBC# | > | 146.0 | 10^2/μL | | | | | |

ANALYZER AND COMPUTER PROGRAM PRODUCT

BACKGROUND OF THE INVENTION

1. Field of the Invention

The present invention relates to an analyzer and a computer program product, and more particularly, it relates to an analyzer capable of analyzing a plurality of types of analytes and a computer program product.

2. Description of the Background Art

An analyzer capable of analyzing a plurality of types of analytes is known in general (refer to U.S. Pat. No. 6,391,263, for example).

The analyzer disclosed in the aforementioned U.S. Pat. No. 6,391,263 varies analytical conditions with the species of animals from which blood samples (analytes) are derived. Therefore, this analyzer can measure blood samples of a plurality of types of animals.

On the other hand, there is a demand in a field of research, for example, for classifying an animal species into minor classifications on the basis of states thereof while analyzing blood samples on the basis of analytical conditions corresponding to the minor classifications respectively. For example, there is a demand for classifying an animal species "rat" into minor classifications such as "healthy rat", "rat developing disease A", "rat developing disease B" etc. while analyzing blood samples on the basis of analytical conditions corresponding to the minor classifications respectively.

However, it is disadvantageously difficult to meet this demand with the analyzer disclosed in the aforementioned U.S. Pat. No. 6,391,263.

SUMMARY OF THE INVENTION

The scope of the present invention is defined solely by the appended claims, and is not affected to any degree by the statements within this summary.

An object of the present invention is to provide an analyzer easily analyzing an analyte on the basis of an analytical condition corresponding to a minor classification prepared by subdividing a major classification of the analyte.

In order to attain the aforementioned object, an analyzer according to a first aspect of the present invention, which is an analyzer capable of analyzing a plurality of types of analytes, comprises major classification selection means for selecting a major classification corresponding to analyte to be analyzed from a plurality of major classifications indicating the types of analytes, displaying means for preferentially displaying minor classifications, belonging to the major classification selected by the major classification selection means, prepared by subdividing the major classification, minor classification selection means for selecting one of the minor classifications displayed by the displaying means, and analysis means for analyzing the analyte to be analyzed on the basis of a first analytical condition corresponding to the minor classification selected by the minor classification selection means.

A computer program product according to a second aspect of the present invention, which is a computer program product capable of analyzing a plurality of types of analytes, comprises first computer code for selecting a major classification corresponding to analyte to be analyzed from a plurality of major classifications indicating the types of analytes, second computer code for preferentially displaying minor classifications, belonging to selected the major classification, prepared by subdividing the major classification, third computer code for selecting one of the displayed minor classifications and fourth computer code for analyzing the analyte to be analyzed on the basis of an analytical condition corresponding to selected the minor classification.

An analyzer according to a third aspect of the present invention, which is an analyzer analyzing an analyte derived from an animal, includes measurement registration accepting means accepting entry of measurement registration information of the analyte and analysis means analyzing the analyte on the basis of the measurement registration information accepted by the measurement registration accepting means, while the measurement registration information includes a category prepared by classifying the animal from which the analyte is derived on the basis of its state.

The foregoing and other objects, features, aspects and advantages of the present invention will become more apparent from the following detailed description of the present embodiment when taken in conjunction with the accompanying drawings.

BRIEF DESCRIPTION OF THE DRAWINGS

FIGS. 4 to 6 illustrate measurement registration screens displayed on a data processing terminal shown in FIG. 1;

FIG. 7 illustrates a category registration screen displayed on the data processing terminal shown in FIG. 1;

FIG. 8 illustrates a flagging determination value set screen displayed on the data processing terminal shown in FIG. 1;

DESCRIPTION OF THE PREFERRED EMBODIMENTS

The preferred embodiment of the present invention is described hereinafter with reference to the drawings. In relation to this embodiment, a blood analyzer for analyzing animal blood is described as an exemplary analyzer according to the present invention.

The structure of the blood analyzer for analyzing animal blood according to the embodiment of the present invention is now described with reference to FIGS. 1 to 3.

Figure 1:
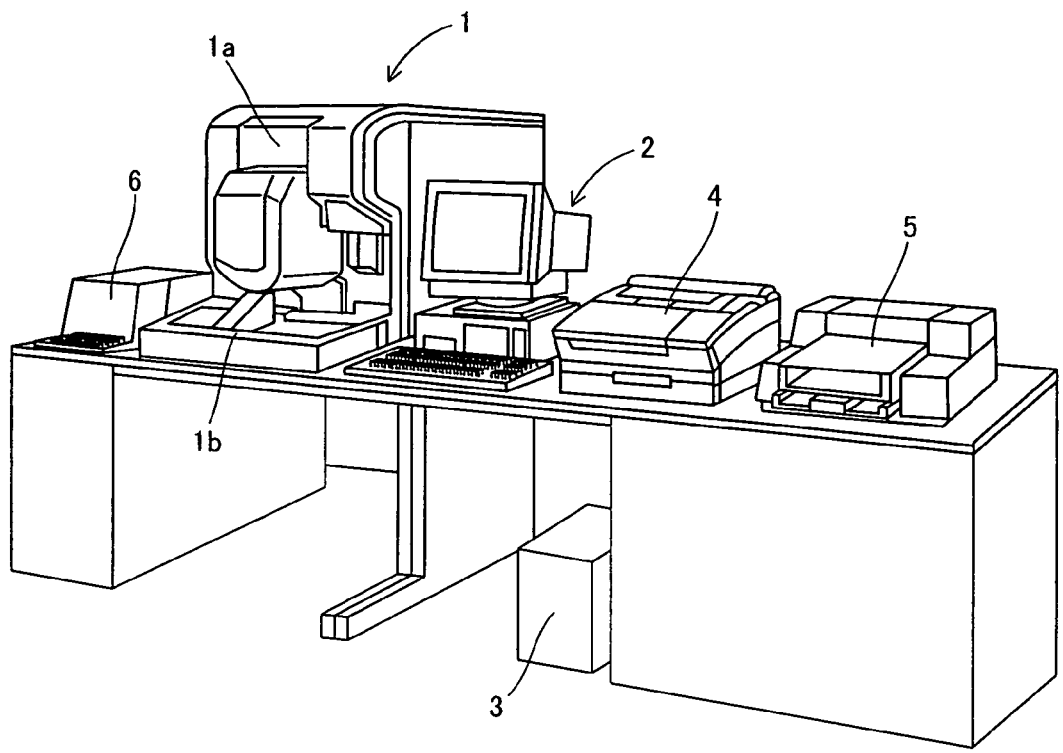
FIG. 1 is a perspective view showing the overall structure of a blood analyzer according to an embodiment of the present invention.

As shown in FIG. 1, the blood analyzer according to this embodiment comprises a measuring apparatus 1, a data processing terminal 2, an air pressure source 3, a page printer 4, a color graphic printer 5 and a data printer 6. The measuring apparatus 1 includes a measuring part 1a detecting signals from blood samples of animals and outputting digital data (raw data) corresponding to the detected signals and a transport part 1b automatically supplying the blood samples to the measuring part 1a. The data processing terminal 2, including a computer (PC), a keyboard, a mouse and a display, has a function of analyzing the digital data received from the measuring part 1a and outputting analysis data as a result of analysis of the blood samples. The air pressure source 3 has a function of generating positive and vacuum pressures used in the measuring part 1a and supplying the positive and vacuum pressures to the measuring part 1a. The page printer 4 is provided for printing a list etc. of the analysis data output from the data processing terminal 2. The color graphic printer 5 is provided for printing scattergrams described later and images appearing on the display of the data processing terminal 2. The data printer 6 is provided for printing the analysis data output from the data processing terminal 2 on cut-form sheets.

Figure 2:
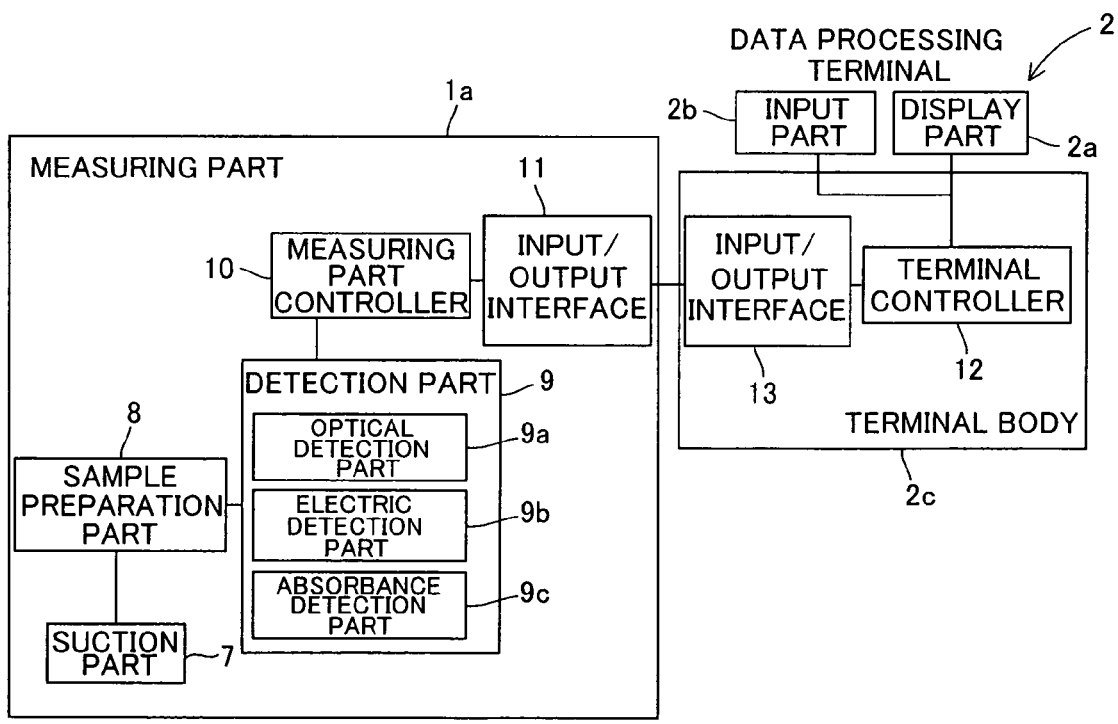
FIG. 2 is a block diagram for illustrating the internal structure of the blood analyzer shown in FIG. 1.

As shown in FIG. 2, the measuring part 1a includes a suction part 7, a sample preparation part 8, a detection part 9, a measuring part controller 10 and an input/output interface 11. The suction part 7 has a function of sucking the blood samples and another function of sucking a reagent employed for measuring the blood samples from a reagent container (not shown). The sample preparation part 8 prepares samples from which signals must be detected through processing such as dilution, hemolysis and staining of the blood samples by mixing the blood samples sucked by the suction part 7 and the reagent with each other. The detection part 9 detects signals from the samples prepared by the sample preparation part 8 and outputs electric signals (analog data) corresponding to the detected signals to the measuring part controller 10. This detection part 9 includes an optical detection part 9a, an electric detection part 9b and an absorbance detection part 9c.

The optical detection part 9a detects signals related to white blood cells (WBC) contained in the samples with a flow cytometer. More specifically, the optical detection part 9a feeds blood cells contained in the blood samples one by one to a flow cell (not shown) for detecting lateral scattered light intensity and lateral fluorescence intensity obtained by irradiating the blood cells with a laser beam.

The electric detection part 9b detects signals related to red blood cells (RBC) and blood platelets (PLT) according to a DC (direct current) detection system. More specifically, the electric detection part 9b detects the magnitudes of impedances between electrodes set on both sides of micropores (not shown) fed with a dc current when cells (red blood cells and blood platelets) pass through the micropores.

The absorbance detection part 9c detects signals related to hemoglobin by irradiating the prepared samples with light.

The measuring part controller 10 includes a CPU, a ROM, a RAM, an A-D converter circuit etc. This measuring part controller 10 creates the aforementioned raw data by digitizing the electric signals output from the detection part 9 in measurement of the blood samples and outputs the same to the data processing terminal 2 through the input/output interface 11. The measuring part controller 10 has a function of controlling operations of the suction part 7, the sample preparation part 8 and the detection part 9.

The data processing terminal 2 includes a display part 2a formed by the display, an input part 2b formed by the mouse and the keyboard and a terminal body 2c formed by the computer. The display part 2a is provided for displaying various information output from the terminal body 2c and operating screens. The input part 2b is provided for inputting prescribed information in the terminal body 2c and allowing various selections on the operating screens displayed on the display part 2a. The terminal body 2c includes a terminal controller 12 and an input/output interface 13. The terminal controller 12 includes a CPU, a ROM, a RAM, an HDD (hard disk drive) etc. This HDD stores animal species from which the blood samples are derived and categories belonging to the animal species in association with each other, as shown in a category table 14 of FIG. 3. The term "category" indicates a minor classification prepared by subdividing an animal from which each blood sample is derived on the basis of its state. For example, minor classifications "mouse standard" and "mouse 001" are employed as the categories of an animal species "mouse". These minor classifications "mouse standard" and "mouse 001" may be employed for a mouse dosed with no prescribed medicament and a mouse dosed with a prescribed medicament respectively, or a healthy rat and a rat developing a prescribed disease respectively, for example.

In the category table 14, a category "rat standard" is associated with the animal species "rat". Further, each category is associated with the lower age limit (0.0 to 999.9) and the upper age limit (0.0 to 999.9) in this category, the unit of the lower and upper age limits (week, month or year) and the sexuality (male, female or either sex). The term "either sex" indicates either male or female.

In the category table 14, in addition, each animal species is associated with positional information indicating a position in a pull-down menu 23b described later.

The HDD of the terminal controller 12 stores a plurality of abnormality determination threshold tables 15 and a plurality of flagging determination value tables 16 as analytical conditions. This HDD stores each determination threshold table 15 and each flagging determination value table 16 in correspondence to each category. A user can set the abnormality determination threshold tables 15 and the flagging determination value tables 16.

Each abnormality threshold table 15 consists of thresholds (lower and upper limits) for determining whether or not analysis data corresponding to measured items are abnormal. In other words, these thresholds define the normal ranges of the analysis data. More specifically, each abnormality determination threshold table 15 is constituted of the lower and upper limits of the analysis data such as the number of white blood cells (WBC), the number of red blood cells (RBC), hemoglobin concentrations (HGB) etc.

When any analysis data falls below the lower limit corresponding thereto, the display part 2a displays an abnormality determination mark (−) indicating that this analysis data is at a warning level below the lower limit along with the analysis data on an analysis data display screen described later. If any analysis data exceeds the upper limit corresponding thereto, on the other hand, the display part 2a displays another abnormality determination mark (+) indicating that the analysis data is at another warning level beyond the upper limit along with the analysis data on the analysis data display screen.

Each flagging determination value table 16 consists of a plurality of flagging determination formulas for determining whether or not it is necessary to output flagging messages as to analysis data. The flagging messages are employed for indicating a possibility that the content, the percentage, the particle size distribution, the state etc. of any blood cell or component contained in each blood sample is abnormal. More specifically, each flagging determination value table 16 is constituted of flagging determination values (NEUT#<10.0×$10^2$/μL, NEUT %<10.0% etc. and LYMPH#>40.0×$10^2$/μL, LYMPH %>50.0% etc.) corresponding to flagging messages such as "Neutropenia", "Lymphocytosis" etc. The flagging messages "Neutropenia" and "Lymphocytosis" indicate decrease of the number of neutrophiles and increase of the number of lymphocytes in the corresponding blood sample respectively. Symbols "NEUT#" and "NEUT %" denote the content and the percentage of neutrophiles in the corresponding blood sample respectively, while symbols "LYMPH#" and "LYMPH %" denote the content and the percentage of lymphocytes in the corresponding blood sample respectively.

The HDD of the terminal controller 12 further stores analytical conditions corresponding to the respective animal species. More specifically, the terminal controller 12 stores partitioning information 80 including partitioning conditions for the scattergram employed for obtaining analysis data every blood cell type by partitioning the scattergram described later.

The structures of the operating screens of the data processing terminal 2 according to this embodiment are now described with reference to FIGS. 2 to 9. The display part 2a of the data processing terminal 2 (see FIG. 2) displays all operating screens shown in FIGS. 4 to 9.

FIG. 4 shows a measurement registration screen employed for accepting measurement registration information of the blood samples. This measurement registration screen is constituted of a sample information selection/input part 17, a sample information display part 18 and a category information display part 19. The sample information selection/input part 17 is provided for selecting and inputting information related to the blood samples. This sample information selection/input part 17 is employed for selecting positions for inputting the information with the mouse of the input part 2b (see FIG. 2) and inputting the information through the keyboard of the input part 2b. The sample information selection/input part 17 is constituted of a sample number entry box 20, a rack number entry box 21, a test tube position entry box 22, an animal species combo box 23, a category combo box 24, a discrete combo box 25 and a sample comment entry box 26.

The sample number entry boxy 20 is provided for inputting sample numbers of the blood samples. The rack number entry box 21 is provided for inputting a rack number decided every rack storing 10 test tubes storing blood samples respectively as a set. The test tube position entry box 22 is provided for inputting any of numbers 1 to 10 as a test tube position number indicating the position of a test tube storing a certain blood sample in the rack.

The animal species combo box 23 is provided for accepting selection of an animal species from which a blood sample to be analyzed is derived from the plurality of animal species. More specifically, the animal species combo box 23 is so formed as to display a list (pull-down menu) 23b of animal species (major classifications) consisting of "rat", "mouse", "rabbit", "dog", "monkey" and "other" when the user clicks an item selection button 23a provided on the right end of the animal species combo box 23 with the mouse, as shown in FIG. 5. The animal species "other" is used for analyzing a blood sample derived from an animal other than the animal species "rat", "mouse", "rabbit", "dog" and "monkey". When the user selects one animal species from the displayed pull-down menu 23b with a click, the animal species combo box 23 displays the selected animal species while closing the pull-down menu 23b.

The pull-down menu 23b has positional information on positions "1", "2", "3", "4", "5" and "6" displaying the animal species "rat", "mouse", "rabbit", "dog", "monkey" and "other" respectively in FIG. 5.

The category combo box 24 is provided for displaying only categories (minor classifications) belonging to the animal species (major classification) selected through the animal species combo box 23 while accepting selection of one category from the displayed ones. More specifically, the category combo box 24 is so formed as to display a list (pull-down menu) 24b of categories when the user clicks an item selection button 24a provided on the right end of the category combo box 24 with the mouse, as shown in FIG. 6. When the user selects one category from the displayed pull-down menu 24b with a click, the category combo box 24 displays the selected category while closing the pull-down menu 24b.

The pull-down menu 23b has positional information on positions "1", "2", "3", "4" and "5" displaying the categories "rat standard", "rat 001", "rat 002", "rat 003" and "rat 004" respectively in FIG. 6.

The pull-down menu 24b displays no categories before the user selects the animal species through the animal species combo box 23. Thus pull-down menu 24b is so formed as to extract only the categories corresponding to the selected animal species from the category table 14 (see FIG. 3) and display the same when the user selects the animal species through the animal species combo box 23. When the user selects the animal species "rat" on the pull-down menu 23b of the animal species combo box 23 as shown in FIG. 3, for example, the categories "rat standard", "rat 001", "rat 002", "rat 003" and "rat 004" belonging to the animal species "rat" are extracted from the category table 14 and displayed on the pull-down menu 24b.

The discrete combo box 25 is provided for accepting selection of a blood sample analysis mode, as shown in FIG. 4. The discrete combo box 25 is so formed as to display a list (pull-down menu) (not shown) of blood sample analysis modes when the user clicks an item selection button 25a provided on the right end of the discrete combo box 25 with the mouse. This pull-down menu displays four analysis modes "CBC", "CBC+DIFF", "CBC+DIFF+RET" and "CBC+RET".

The mode "CBC" is an analysis mode for calculating the numbers of red blood cells, white blood cells and platelets. The mode "DIFF" is an analysis mode for analyzing five types of white blood cells, i.e., lymphocytes, monocytes, eosinophiles, neutrophiles and basophiles. The mode "RET" is an analysis mode for analyzing reticulocytes. In the analysis mode "CBC+DIFF", therefore, the analyzer calculates the numbers of red blood cells, white blood cells and platelets while analyzing lymphocytes, monocytes, eosinophiles, neutrophiles and basophiles. In the analysis mode "CBC+DIFF+RET", on the hand, the analyzer calculates the numbers of red blood cells, white blood cells and platelets while analyzing lymphocytes, monocytes, eosinophiles, neutrophiles and basophiles as well as reticulocytes. In the analysis mode "CBC+RET", further, the analyzer calculates the numbers of red blood cells, white blood cells and platelets while analyzing reticulocytes.

The discrete combo box 25 is so formed as to display a selected analysis mode while closing the pull-down menu when the user selects the analysis mode from those displayed on the pull-down menu with a click.

The user inputs comments related to the blood sample through the sample comment entry box 26.

The sample information display part 18 displays information related to each blood sample. In other words, the sample information display part 18 displays information consisting of "sample number", "category", "animal species", "discrete" (analysis mode), "rack number", "test tube position number", "status" and "sample comment" every blood sample. The information "status" indicates the state ("COMP", "PEND" or "ERR") of analysis of the blood sample. Symbol "COMP" denotes completion of the analysis of the blood sample. Symbol "PEND" denotes pendency of the analysis of the blood sample. Symbol "ERR" denotes an error caused in the analysis of the blood sample.

The category information display part 19 is so formed as to display category information (attribute information) corresponding to the selected category when the user selects this category in the category combo box 24. This category information display part 19 is constituted of a category name display box 27, an animal species display box 28, a sexuality display box 29, an age unit display box 30, a lower age limit display box 31 and an upper age limit display box 32. The category name display box 27, the animal species display box 28, the sexuality display box 29, the age unit display box 30, the lower age limit display box 31 and the upper age limit display box 32 display the category name, the animal species, the sexuality, the age unit, the lower age limit and the upper age limit corresponding to the category selected through the category combo box 24 and read from the category table 14 (see FIG. 3).

FIG. 7 shows a category registration screen. The user can previously register any category on this category registration screen before analyzing blood samples. This category registration screen is constituted of a category registration part 33 for registering the category and a category display part 34 displaying information on the category registered through the category registration part 33. The category registration part 33 is formed by a category name entry box 35, an animal species combo box 36, an upper age limit entry box 37, a lower age limit entry box 38, an age unit combo box 39, a sexuality combo box 40 and a comment entry box 41.

The category name entry box 35 is provided for inputting the category name. This category name can be formed by an arbitrary name such as a combination of the name of the animal species and a mark or an alphabetical combination.

The animal species combo box 36 is formed similarly to the animal species combo box 23 (see FIG. 5) in the aforementioned measurement registration screen. The upper age limit entry box 37 and the lower age limit entry box 38 are provided for inputting the upper and lower age limits in the category introduced into the category name entry box 35 respectively. The age unit combo box 39 is provided for setting the unit of the aforementioned upper and lower age limits. This age unit combo box 39 displays a list (pull-down menu) (not shown) of units consisting of "week", "month" and "year" when the user clicks an item selection button 39*a* provided on the right end thereof. When the user selects (clicks) one unit on this pull-down menu, the age unit combo box 39 displays the selected unit and closes the pull-down menu.

The sexuality combo box 40 is provided for setting the sexuality of the category introduced into the category name entry box 35. This sexuality combo box 40 displays a list (pull-down menu) (not shown) of sexuality consisting of "male", "female" and "either sex" when the user clicks an item selection button 40*a* provided on the right end thereof. When the user selects (clicks) one sexuality on the pull-down menu, the sexuality combo box 40 displays the selected sexuality and closes the displayed pull-down menu. The comment entry box 41 is provided for inputting comments corresponding to the category introduced into the category name entry box 35 if necessary. The contents of the category registered through the category name entry box 35, the animal species combo box 36, the upper age limit entry box 37, the lower age limit entry box 38, the age unit combo box 39, the sexuality combo box 40 and the comment entry box 41 are displayed on the category display part 34 in the form of a table, and stored in the category table 14 shown in FIG. 3.

FIG. 8 shows a flagging determination value set screen. The user sets flagging determination formulas in the flagging determination value table 16 (see FIG. 3) corresponding to each category on this flagging determination value set screen. The flagging determination value set screen is provided with a category combo box 42, an animal species display box 43, an age unit display box 44, a sexuality display box 45, a lower age limit display box 46, an upper age limit display box 47 and a flagging determination value set part 48. The category combo box 42 has a structure similar to that of the category combo box 24 (see FIG. 6) of the aforementioned measurement registration screen. The animal species display box 43, the age unit display box 44, the sexuality display box 45, the lower age limit display box 46 and the upper age limit display box 47 are so formed as to display the animal species, the age unit, the sexuality, the lower age limit and the upper age limit read from the category table 14 (see FIG. 3) in correspondence to the category selected through the category combo box 42 respectively.

The flagging determination formula set part 48 is so formed that the user can set a proper flagging determination formula every type of blood cell such as white blood cells (WBC), red blood cells (RBC) or reticulocytes (RET). The user sets flagging determination formulas on the flagging determination value set part 48 by inputting desired numerical values in numerical entry boxes 48*b* corresponding to flagging messages 48*a* respectively. If the user inputs "10.0" in the numerical entry box 48*b* corresponding to the flagging message 48*a* "Neutropenia" (decrease of the number of neutrophiles), for example, the flagging determination set part 48 displays the flagging message "Neutropenia" when the content "NEUT#" or the percentage "NEUT %" of neutrophiles is less than $10.0 \times 10^2/\mu L$ or 10.0%. The flagging determination set part 48 is also provided with check boxes 48*c* in correspondence to the flagging messages 48*a* respectively. When the user clicks any check box 48*c*, the flagging determination formula set part 48 determines flagging related to the corresponding flagging message 48*a*, and vice versa.

Figure 9:
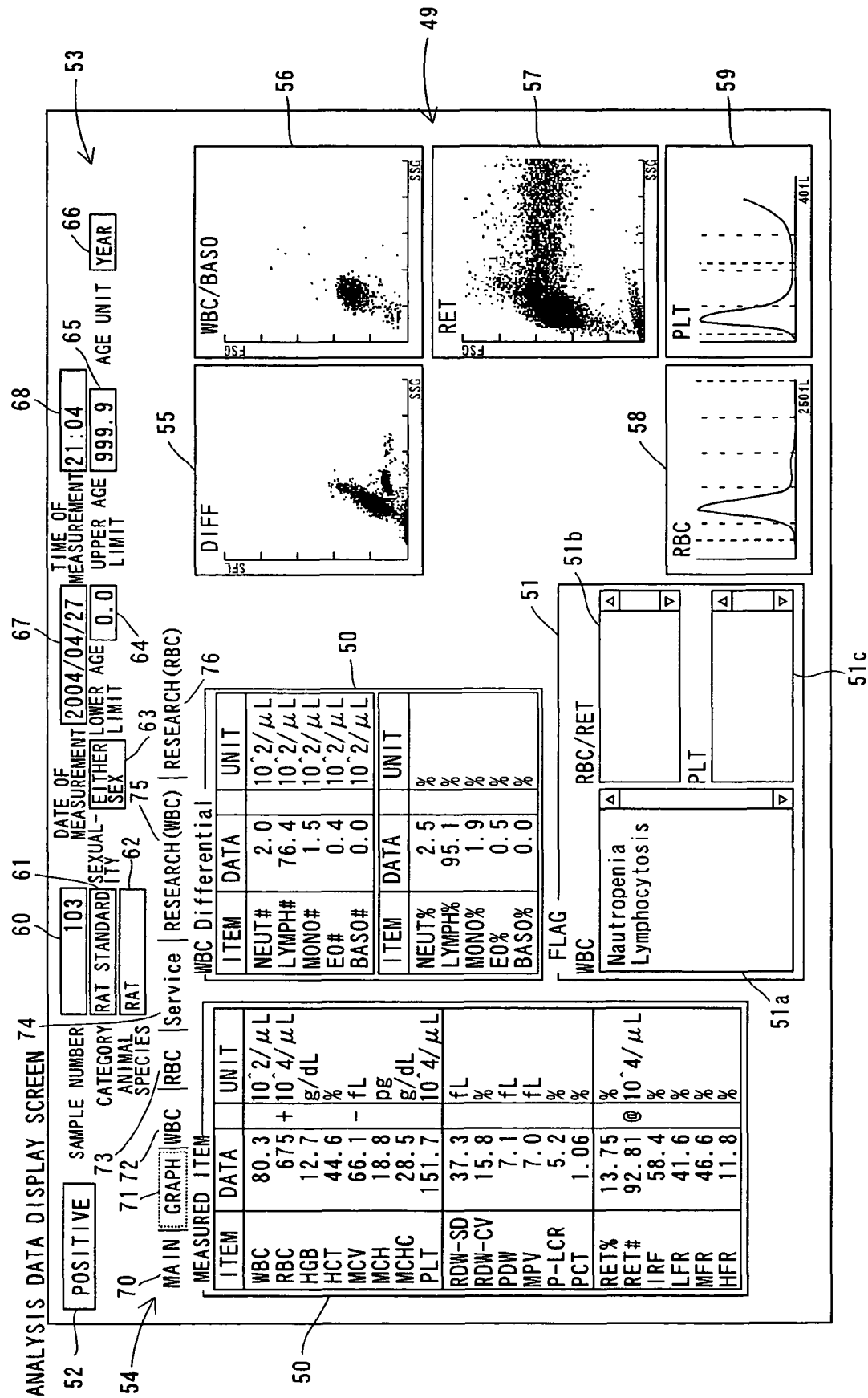
FIG. 9 is an analysis data display screen displayed on the data processing terminal shown in FIG. 1.

FIG. 9 shows an analysis data display screen for displaying analysis data of each blood sample. This analysis data display screen is constituted of a graph display part 49, an analysis data display part 50, a flagging message display part 51, a flag status display part 52, a sample information display part 53 and a switching tag display part 54. The graph display part 49 is constituted of a DIFF scattergram 55, a WBC/BASO scattergram 56, an RET scattergram 57, an RBC particle size distribution chart 58 and a PLT particle size distribution chart 59. The DIFF scattergram 55 is employed for classifying five types of white blood cells, i.e., lymphocytes (LYMPH), monocytes (MONO), eosinophiles (EO), neutrophiles (NEUT) and basophiles (BASO). The WBC/BASO scattergram 56 is employed for classifying basophiles (BASO), mononuclear lymphocytes (LYMPH+MONO) and polynuclear lymphocytes (NEUT+EO) other than basophiles. The RET scattergram 57 is employed for classifying reticulocytes (RET). In each of the DIFF, WBC/BASO and RET scattergrams 55, 56 and 57, the axes of abscissas and ordinates show lateral scattered light intensity and lateral fluorescence intensity detected by the optical detection part 9*a* respectively. The terminal controller 12 creates the scattergrams 55, 56 and 57 and the distribution charts 58 and 59 on the basis of the raw data transmitted from the measuring part 1*a*.

The RBC and PLT particle size distribution charts 58 and 59 show particle size distributions of red blood cells (RBC) and platelets (PLT) respectively.

The analysis data display part 50 displays analysis data acquired by the terminal controller 12 on the basis of the DIFF, WBC/BASO and RET scattergrams 55, 56 and 57 and the distribution charts 58 and 59 every measured item.

The flagging message display part 51 is provided for displaying flagging messages. This flagging message display part 51 is constituted of a white blood cell flagging message display part 51*a* displaying flagging messages related to white blood cells (WBC), a red blood cell flagging message display part 51*b* displaying flagging messages related to red blood cells (RBC) and reticulocytes (RET) and a platelet flagging message display part 51c displaying flagging messages related to platelets (PLT). The flag status display part 52 displays a flag status "POSITIVE" when the flagging message display part 51 displays flagging messages, while displaying a flag status "NEGATIVE" when the flagging message display part 51 displays no flagging messages.

The sample information display part 53 displays information related to the analyzed blood sample. This sample information display part 53 is constituted of a sample number display part 60, a category display part 61, an animal species display part 62, a sexuality display part 63, a lower age limit display part 64, an upper age limit display part 65, an age unit display part 66, a measuring date display part 67 and a measuring time display part 68. The sample number display part 60 displays the sample number of the blood sample. The category display part 61 displays the category selected through the category combo box 24 (see FIG. 4) of the measurement registration screen. The animal species display part 62 displays the animal species selected through the animal species combo box 23 (see FIG. 4) of the measurement registration screen. The sexuality display part 63 displays the sexuality corresponding to the selected category. The lower and upper age limit display parts 64 and 65 display the upper and lower age limits of the animal species corresponding to the selected category respectively. The age unit display part 66 displays the unit of the lower and upper age limits. The measuring date display part 67 and the measuring time display part 68 display the date and the time of measurement of the blood sample respectively.

The switching tag display part 54 is provided for switching the display formats of the scattergrams 55, 56 and 57 and the analysis data displayed on the graph display part 49 and the analysis data display part 50 respectively. The switching tag display part 54 is formed by a main tag 70, a graph tag 71, a WBC tag 72, an RBC tag 73, a service tag 74, a research (WBC) tag 75 and another research (RBC) tag 76. The main tag 70 is employed for displaying analysis data and scattergrams as to principal measured items. The graph tag 71 is employed for displaying all analysis data, scattergrams and particle size distribution charts obtained by measuring blood samples. The WBC tag 72 is employed for displaying analysis data and scattergrams related to white blood cells. The RBC tag 73 is employed for displaying analysis data and scattergrams related to red blood cells. The service tag 74 is employed for displaying prescribed service data. The research (WBC) tag 75 is employed for displaying analysis data and scattergrams related to prescribed research items on white blood cells. The research (RBC) tag 76 is employed for displaying analysis data and scattergrams related to prescribed research items on red blood cells. On the analysis data display screen shown in FIG. 9, the graph tag 71 is so selected that the graph display part 49 and the numerical data display part 50 display all analysis data, scattergrams and particle size distribution charts obtained by measuring blood samples.

Processing executed by the terminal controller 12 for measuring a certain blood sample with the blood analyzer according to the embodiment of the present invention is now described with reference to FIGS. 2 to 6 and 9 to 13.

Figure 10:
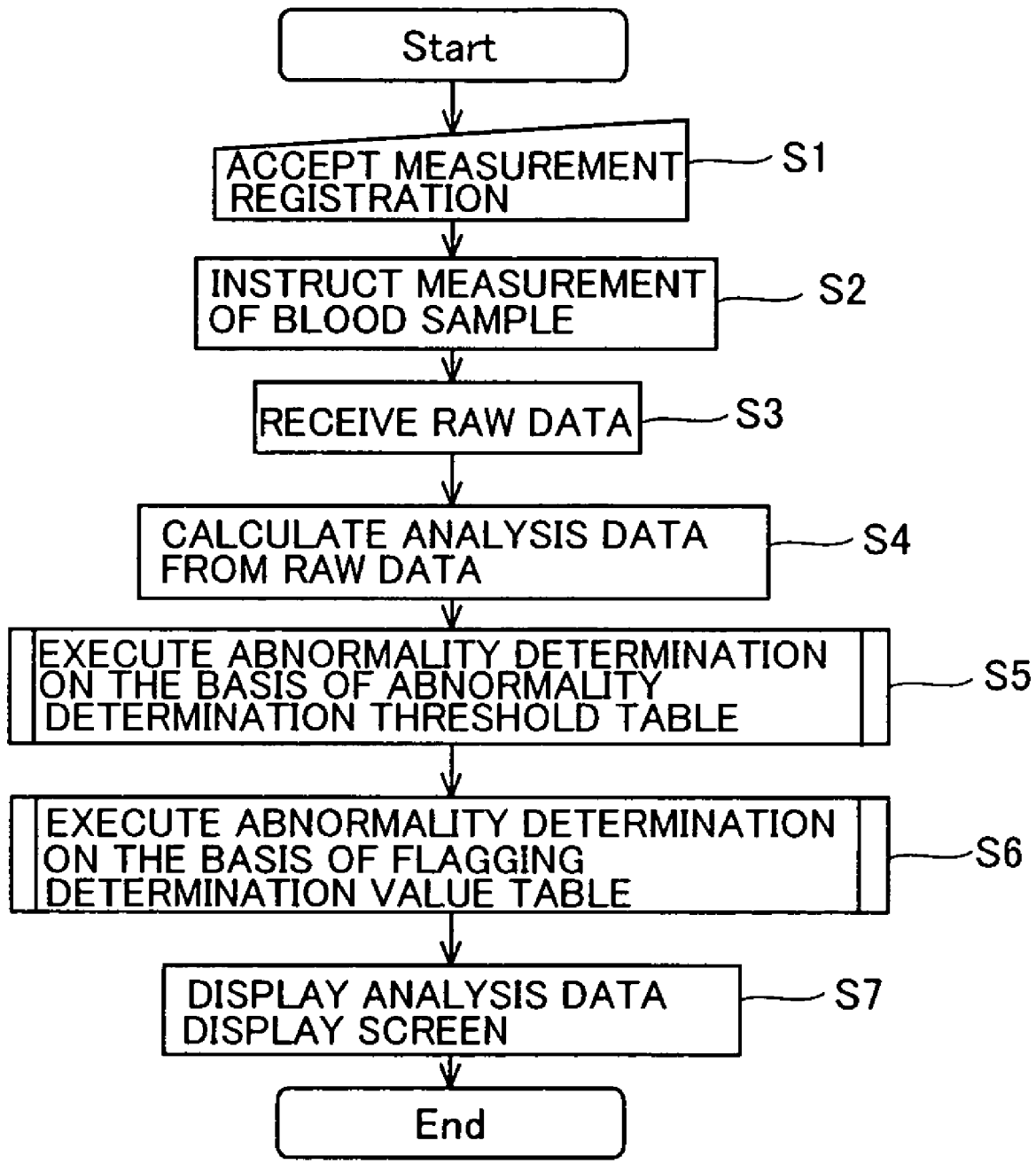
FIG. 10 is a flow chart for schematically illustrating processing carried out by a terminal controller 12 for measuring a blood sample.
Figure 11:
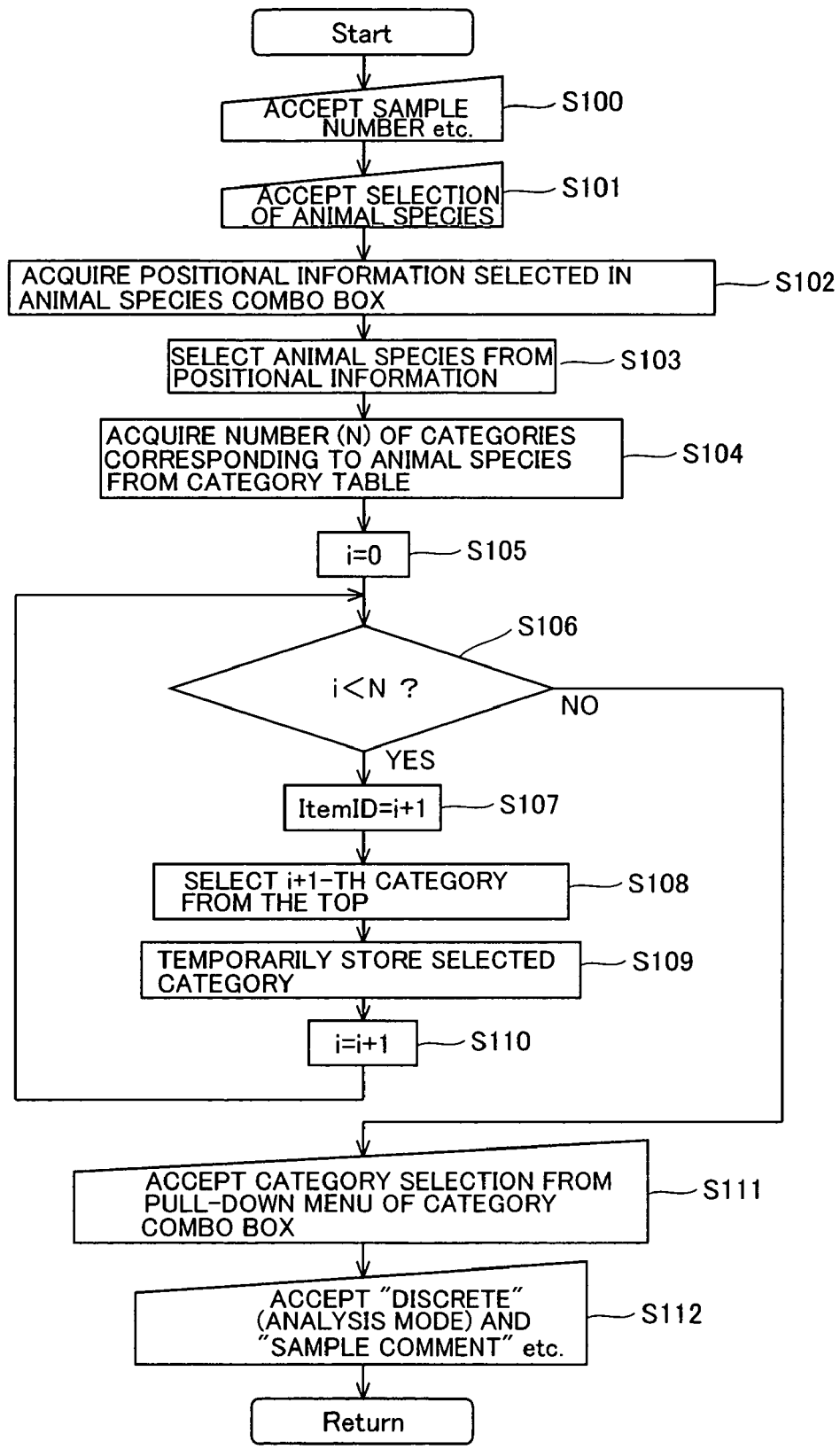
FIG. 11 is a flow chart for illustrating processing at a step S1 in the flow chart shown in FIG. 10.

The processing executed by the terminal controller 12 for measuring the blood sample consists of operations of steps S1 to S7, as shown in FIG. 10. At the step S1, the terminal controller 12 accepts entry of measurement registration information with the measurement registration screen (see FIG. 4). The processing of this step S1 consists of steps S100 to S111, as shown in FIG. 11.

At the step S100, the terminal controller 12 accepts entry of the sample number, the rack number and the test tube position in the sample number entry box 20, the rack number entry box 21 and the test tube position entry box 22 respectively.

At the step S101, the terminal controller 12 accepts selection of the animal species through the animal species combo box 23 (see FIG. 5) of the measurement registration screen. More specially, the terminal controller 12 displays the pull-down menu 23b and accepts selection (click) of one animal species on the pull-down menu 23b when the user clicks the item selection button 23a (see FIG. 5) of the animal species combo box 23.

Upon this selection of the animal species, the animal species, the terminal controller 12 accepts position information in the pull-down menu 23b corresponding to the selected animal species at the step S102. The terminal controller 12 the position information "1" when the selected animal species is "rat", or acquires the position information "2" when the selected animal is "mouse", for example.

At the step S103, the terminal controller 12 selects the animal species corresponding to the position information acquired at the step S102 from the category table 14.

At the step S104, the terminal controller 12 acquires the number (N) of the categories belonging to the selected animal species from the category table 14. When the user selects the animal species "rat" on the pull-down menu 23b, for example, the terminal controller 12 acquires the number N (=5) of all categories ("rat standard", "rat 001", "rat 002", "rat 003" and "rat 004") belonging to the animal species "rat" from the category table 14.

At the step S105, the terminal controller 12 initializes i to "0". At the step S106, the terminal controller 12 compares i with the number N acquired at the step S104. The terminal controller 12 advances to the step S111 if i is greater than or equal to N, while advancing to the step S107 if i is less than N.

At the step S107, the terminal controller 12 sets an item ID for identifying the category to "i+1".

At the step S108, the terminal controller 12 selects the $(i+_1)^{th}$ category from the top among the categories belonging to the selected animal species.

At the step S109, the terminal controller 12 temporarily stores the category selected at the step S108 for displaying this category on a position "i+1" of the pull-down menu 24b. The terminal controller 12 displays the stored category on the position "i+1" of the pull-down menu 24b when displaying the pull-down menu 24b.

In processing of the first category, for example, i=0, i.e., item ID=1, and hence the terminal controller 12 stores the category selected at the step S108 in order to display this category on a position "1" of the pull-down menu 24b.

At the step S110, the terminal controller 12 sets i+1 on i and returns to the step S106.

The terminal controller 12 repeats the aforementioned processing of the steps S106 to S110 until i is not less than N (i=N). Thus, the terminal controller 12 temporarily stores all categories of the number N acquired at the step S104, in order to display the same on the pull-down menu 24b.

At the step S111, the terminal controller 12 accepts selection of a single category on the pull-down menu 24b. When the user clicks the item selection button 24a of the category combo box 24 in this processing, the terminal controller 12 displays the pull-down menu 24b of all categories stored at the step S102, and accepts selection (click) of the single category from the displayed pull-down menu 24b. When the user selects the single category, the terminal controller 12 displays the selected category and closes the displayed pull-down menu 24b. When the user selects the single category in this way, the terminal controller 12 selects the single category and temporarily stores it.

The terminal controller 12 skips the step S111 when the user selects no category.

At the step S112, the terminal controller 12 accepts "discrete" (analysis mode) and "sample comment", and returns to processing of the step S2 (see FIG. 10).

At the step S2, the terminal controller 12 transmits a signal instructing the measuring part 1a to start measuring the blood sample. The terminal controller 12 executes this processing for instructing starting of the measurement when the user clicks a start button (not shown) displayed on the display part 2a with the mouse.

According to this instruction, the measuring part 1a processes the blood sample and transmits acquired digital data (raw data) from the measuring part controller 10 to the terminal controller 12.

At the step S3, the terminal controller 12 receives the raw data from the measuring part controller 10.

At the step S4, the terminal controller 12 creates the DIFF scattergram 55 (see FIG. 9), the WBC/BASO scattergram 56, the RET scattergram 57, the RBC particle size distribution chart 58 and the PLT particle size distribution chart 59 on the basis of the raw data acquired at the step S3. The terminal controller 12 acquires analysis data such as the number (WBC) of white blood cells and the number (RBC) of red blood cells by analyzing the scattergrams 55, 56 and 57 and the particle size distribution charts 58 and 59.

In order to analyze the scattergrams 55, 56 and 57, the terminal controller 12 obtains analysis data by partitioning the scattergrams 55, 56 and 57 according to partitioning conditions included in the partitioning information 80 corresponding to the animal species acquired at the step S101.

Figure 3:
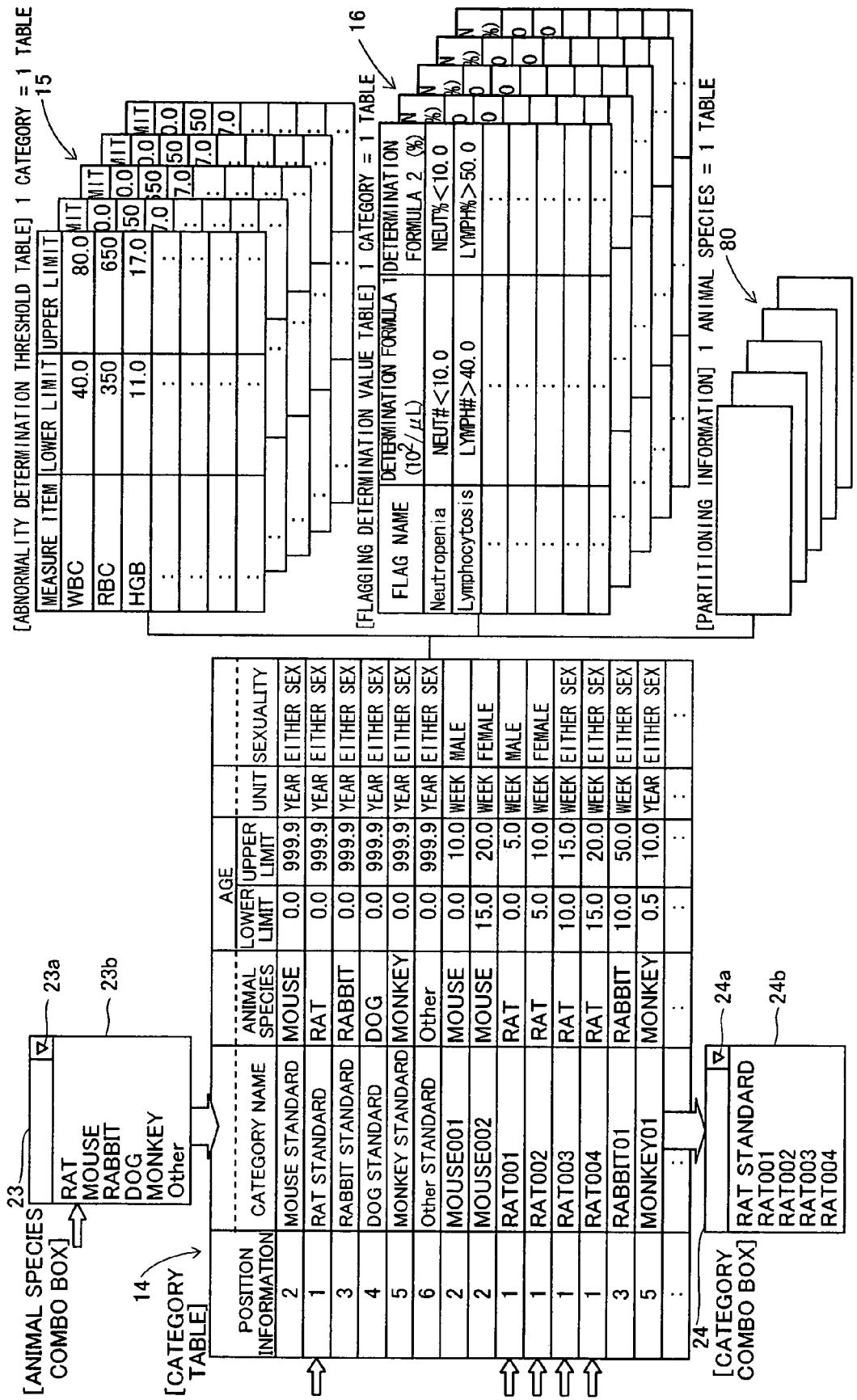
FIG. 3 is a diagram for illustrating information and functions stored in a terminal controller of the blood analyzer shown in FIG. 1.
Figure 12:
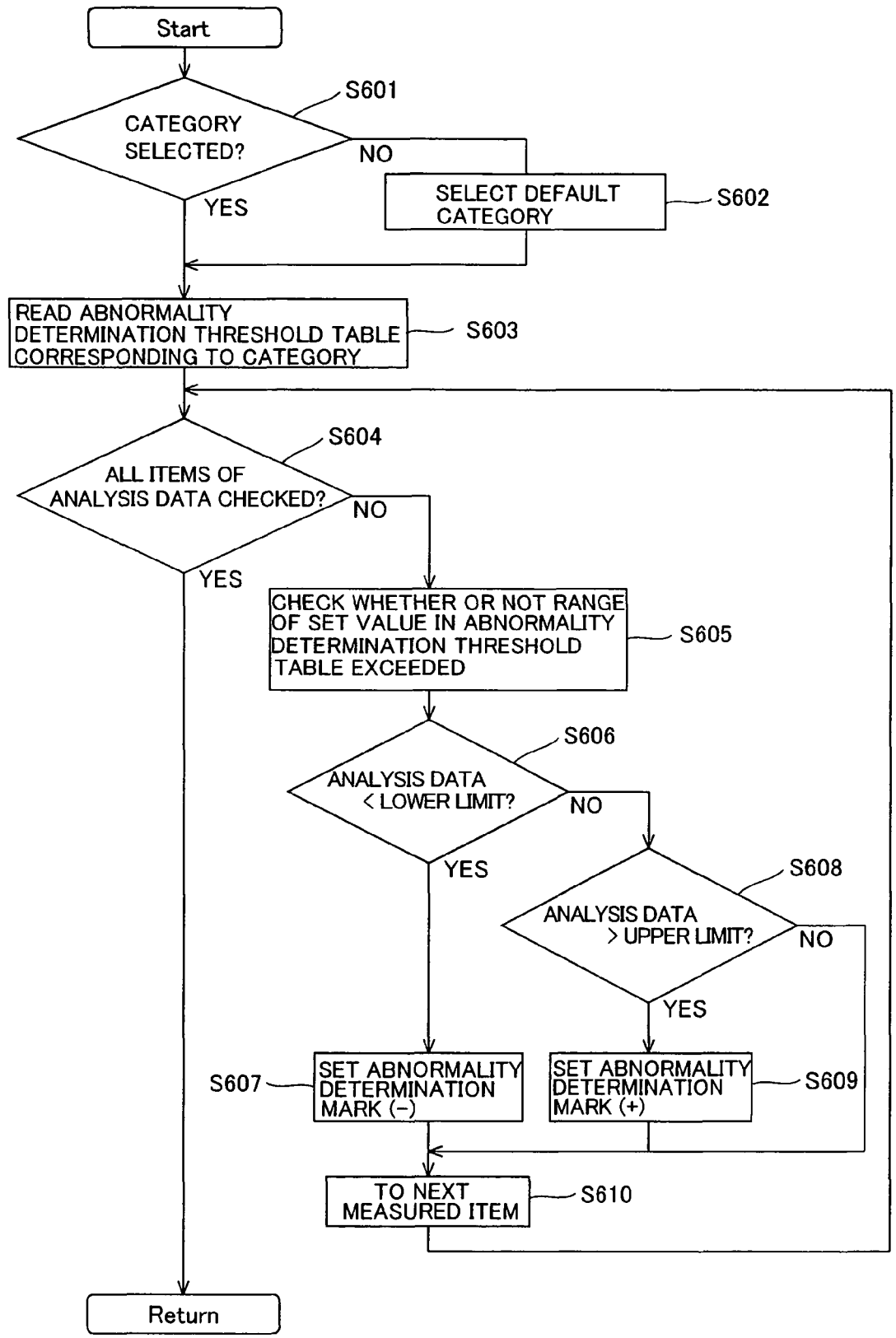
FIG. 12 is a flow chart for illustrating processing at a step S5 in the flow chart shown in FIG. 10.

At the step S5, the terminal controller 12 performs abnormality determination on the analysis data on the basis of the abnormality determination threshold table 15 (see FIG. 3). This processing of abnormality determination consists of steps S601 to S610, as shown in FIG. 12.

At the step S601, the terminal controller 12 determines whether or not the category has been selected at the step S111. The terminal controller 12 advances to the step S603 when the category has been selected, while advancing to the step S602 when no category has been selected. At the step S602, the terminal controller 12 selects a default category, i.e., a standard category corresponding to each animal species. For example, the default category corresponding to the animal species "rat" is "rat standard" and that corresponding to the animal species "mouse" is "mouse standard" in the category table 14 shown in FIG. 3.

At the step S603, the terminal controller 12 reads the abnormality determination threshold table 15 (see FIG. 3) corresponding to the selected category. At the step S604, the terminal controller 12 determines whether or not abnormality determination has been performed as to all measured items. The terminal controller 12 returns to the next step S6 (see FIG. 10) when the analysis data have been subjected to abnormality determination as to all measured items, while advancing to the step S605 when the analysis data have not yet been subjected to abnormality determination as to all measured items. At the step S605 and the subsequent steps, the terminal controller 12 determines whether or not the analysis data as to prescribed measured items exceed the ranges of the set values (thresholds) in the abnormality determination threshold table 15.

At the step S606, the terminal controller 12 determines whether or not analysis data as to a prescribed measured item is less than the corresponding lower limit in the abnormality threshold table 15. When the analysis data as to the prescribed measured item is less than the lower limit, the terminal controller advances to the step S607. When the analysis data as to the prescribed measured item is not less than the lower limit, on the other hand, the terminal controller advances to the step S608. At the step S607, the terminal controller 12 sets the abnormality determination mark (−), and thereafter advances to the step S610.

At the step S608, the terminal controller 12 determines whether or not the analysis data as to the prescribed measured item is greater than the corresponding upper limit in the abnormality threshold table 15. When the analysis data as to the prescribed measured item is greater than the upper limit, the terminal controller sets the abnormality determination mark (+) at the step S609, and thereafter advances to the step S610. When the analysis data as to the prescribed measured item is not greater than the upper limit, on the other hand, the terminal controller advances to the step S610.

At the step S610, the terminal controller 12 shifts the object of abnormality determination to a next measured item. Then, the terminal controller 12 determines whether or not abnormality determination has been performed as to all measured items again. The terminal controller 12 repeats the aforementioned steps S604 to S610 until the same completes abnormality determination as to all measured items.

Figure 13:
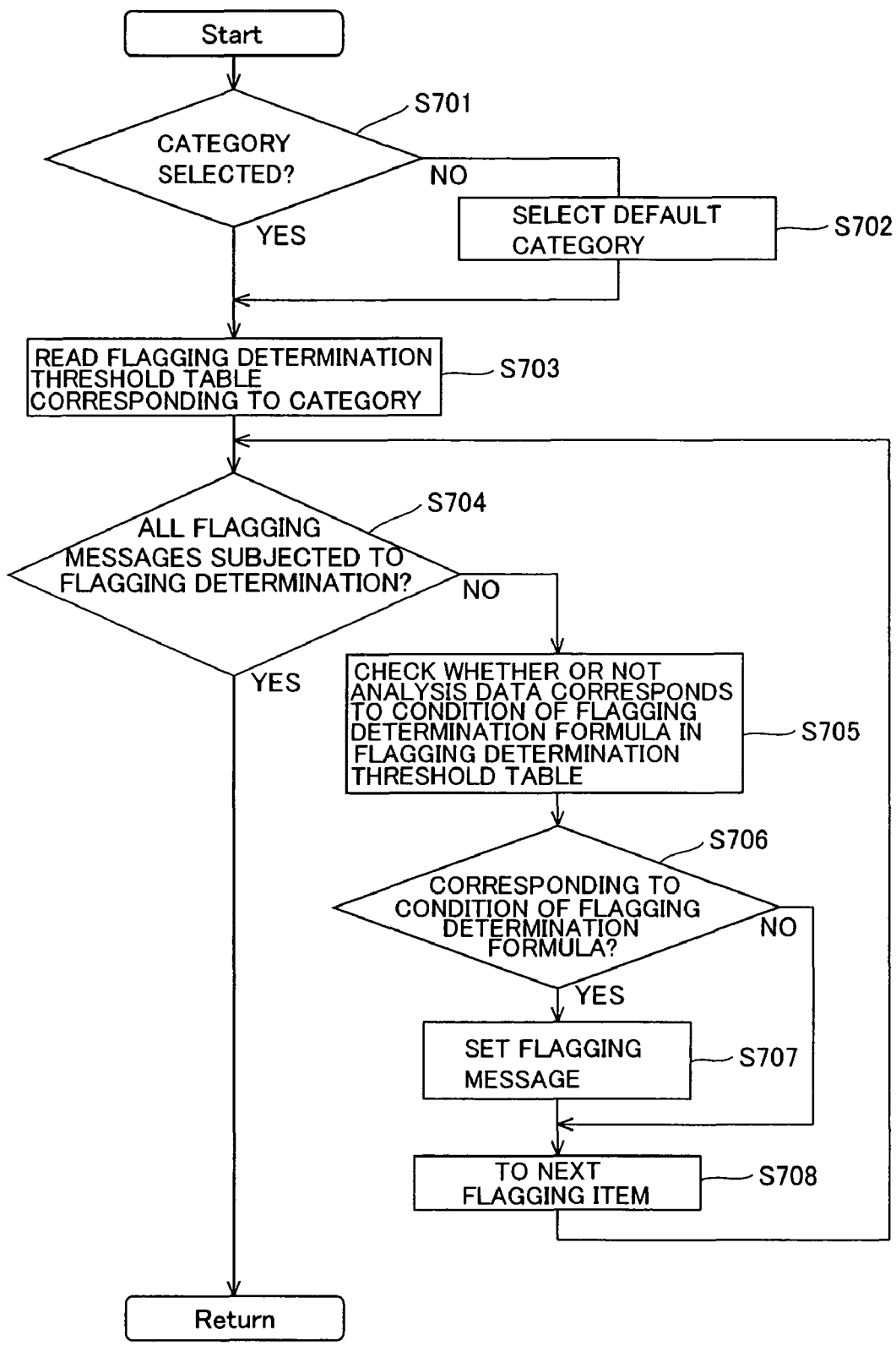
FIG. 13 is a flow chart for illustrating processing at a step S6 in the flow chart shown in FIG. 10.

At the step S6 shown in FIG. 10, the terminal controller 12 performs flagging determination on the analysis data on the basis of the flagging determination value table 16 (see FIG. 3). The processing of this flagging determination consists of steps S701 to S708, as shown in FIG. 13. At the step S701, the terminal controller 12 determines whether or not the category has been selected at the step S111. The terminal controller advances to the step S703 if the category has been selected, while advancing to the step S702 when no category has been selected. At the step S702, the terminal controller 12 selects the default category. The processing at the steps S701 and S702 is similar to hat of the aforementioned steps S601 (see FIG. 12) and S602.

At the step S703, the terminal controller 12 reads the flagging determination value table 16 (see FIG. 3) corresponding to the selected category. At the step S704, the terminal controller 12 determines whether or not flagging determination has been completed as to all flagging messages. More specifically, the terminal controller 12 determines whether or not all flagging messages clicked in the check boxes 48c have been subjected to flagging determination on the flagging determination value set screen (see FIG. 8). The terminal controller 12 returns to the step S7 (see FIG. 10) when all flagging messages have been subjected to flagging determination, while advancing to the step S705 when not all flagging messages have been subjected to flagging determination. At the step S705 and subsequent steps, the terminal controller 12 determines whether or not the analysis data correspond to the conditions of the flagging determination formulas in the flagging determination value table 16 (see FIG. 3).

At the steps S705 and S706, the terminal controller 12 determines whether or not the analysis data corresponds to the condition of each flagging determination formula. As to the flagging item "Neutropenia" in the flagging determination value table 16 shown in FIG. 3, for example, the terminal controller 12 determines whether or not the analysis data corresponds to the following flagging determination value:

*NEUT#* (content of neutrophiles in the blood sample) <10.0×10²/μL or

NEUT % (percentage of neutrophiles in the blood sample)<10.0%

When the analysis data corresponds to the condition of the flagging determination value, the terminal controller 12 advances to the step S707. When the analysis data does not correspond to the condition of the flagging determination value, on the other hand, the terminal controller 12 advances to the step S708. At the step S707, the terminal controller 12 reads the flagging message corresponding to the condition of the flagging determination formula from the flagging determination value table 16 and sets the same. At the step S708, the terminal controller 12 shifts the object of flagging determination to the next flagging message. At the step S704, the terminal controller 12 determines whether or not all flagging messages to be determined have been completely subjected to flagging determination. The terminal controller 12 repeats the aforementioned steps S704 to S708 until the same completes flagging determination as to all flagging messages.

Finally, the terminal controller 12 displays the scattergrams 55, 56 and 57 and the analysis data on the graph display part 49 (see FIG. 9) and the analysis data display part 50 at the step S7, as shown in FIG. 10. At this time, the graph display part 49 displays the DIFF scattergram 55, the WBC/BASO scattergram 56, the RET scattergram 57, the RBC particle size distribution chart 58 and the PLT particle size distribution chart 59. The analysis data display part 50 displays the analysis data obtained by analyzing the DIFF scattergram 55, the WBC/BASO scattergram 56, the RET scattergram 57, the RBC particle size distribution chart 58 and the PLT particle size distribution chart 59 and the abnormality determination mark (−) or (+) set at the step S607 or S609 (see FIG. 12) alongside of each other. The flagging message display part 51 displays the flagging messages set at the step S707 (see FIG. 13) while the flag status display part 52 displays the flag status "POSITIVE".

According to this embodiment, as hereinabove described, the blood analyzer, provided with the terminal controller 12 preferentially displaying the categories (minor classifications) belonging to the selected animal species (major classification), i.e., displaying only the categories belonging to the selected animal species, displaying the pull-down menu 24*b* for accepting selection of the corresponding one of the displayed categories on the display part 2*a* and analyzing the analysis data on the basis of the abnormality determination threshold table 15 and the flagging determination value table 16 corresponding to the category selected on the pull-down menu 24*b*, can perform abnormality determination and flagging determination on the analysis data with the abnormality determination threshold table 15 and the flagging determination value table 16 corresponding to the category prepared by classifying the animal from which the blood sample is derived on the basis of its state.

According to this embodiment, further, the blood analyzer is provided with the pull-down menu 24*b* selectively displaying only the categories (minor classifications) belonging to the selected animal species (major classification) for displaying only the categories belonging to the animal species selected by the user, whereby the user can select a desired one from a small number of categories dissimilarly to a case of selectively displaying a large number of categories regardless of animal species. Thus, the user can easily select the category.

Although the present invention has been described and illustrated in detail, it is clearly understood that the same is by way of illustration and example only and is not to be taken by way of limitation, the spirit and scope of the present invention being limited only by the terms of the appended claims.

For example, while the above embodiment has been described with reference to the blood analyzer for analyzing animal blood as an exemplary analyzer according to the present invention, the present invention is not restricted to this but is also applicable to an analyzer other than the blood analyzer for analyzing animal blood. The present invention may be applied to a blood analyzer for analyzing human blood, for example. In this case, "male" and "female" may be applied as major classifications, while "normal", "patient developing disease A" and "patient developing disease B" belonging to "male" and "normal", "patient developing disease C" and "patent developing disease D" belonging to "female" may be applied as minor classifications.

While the blood analyzer according to the aforementioned embodiment varies the method of partitioning the scattergrams with the major classifications (animal species), the present invention is not restricted to this but the blood analyzer may alternatively vary the method of partitioning the scattergrams with the minor classifications (categories).

While the present invention is applied to the blood analyzer for analyzing blood in the aforementioned embodiment, the present invention is not restricted to this but is also applicable to another analyzer for analyzing an analyte other than blood. For example, the present invention is also applicable to a urinalysis apparatus for analyzing urine.

While the animal species (major classifications) are constituted of "rat", "mouse", "rabbit", "dog", "monkey" and "other" in the aforementioned embodiment, the present invention is not restricted to this but animal species other than the above can also be employed.

While the measuring part and the data processing terminal (data processing part) are provided independently of each other in the aforementioned embodiment, the present invention is not restricted to this but the functions of the data processing terminal may alternatively be built into the measuring part.

While the blood analyzer is so formed as to display only the categories belonging to the selected animal species on the pull-down menu 24*b* when the user selects the animal species according to the aforementioned embodiment, the present invention is not restricted to this but the blood analyzer may alternatively be so formed as to display the categories belonging to the selected animal species and categories common to a plurality of animal species including the selected animal species on the pull-down menu 24*b* when the user selects the animal species, for example. More specifically, the blood analyzer may be provided with a category "mouse/rat standard" common to the animal species "mouse" and "rat" for displaying the common category "mouse/rat standard" on the pull-down menu 24*b* when the user selects the animal species "mouse" or "rat" through the animal species combo box.

While the blood analyzer is so formed as to display only the categories belonging to the selected animal species on the pull-down menu 24*b* when the user selects the animal species in the aforementioned embodiment, the present invention is not restricted to this but the blood analyzer may alternatively display both of the categories belonging to the selected animal species and those not belonging to the selected animal species so far as the same preferentially displays the categories belonging to the selected animal species. In this case, the blood analyzer may display the categories belonging to the selected animal species on the upper half (positions having small numerical values of the positional information) of the pull-down menu 24*b* while displaying those not belonging to the selected animal species on the lower half (positions having large numerical values of the positional information), or may display the categories belonging to the selected animal species with large fonts while displaying those not belonging to the selected animal species with small fonts.

While the blood analyzer is so formed as to accept selection of the animal species through the animal species combo box 23 in the aforementioned embodiment, acceptance of selection of the animal species (major classification) in the present invention is not restricted to this but the blood analyzer may alternatively accept selection of the animal species inputted through the keyboard, similarly to the sample number entry box 20. Alternatively, a bar code including information of the corresponding animal species may be attached to the test tube storing the corresponding blood sample so that the blood analyzer accepts selection of the animal species by reading the bar code with a bar code reader. Further alternatively, the blood analyzer may accept selection of the animal species by receiving the information of the animal species from a host computer along with the sample number etc.

What is claimed is:

1. A blood cell analyzer for analyzing a blood sample of an animal, the blood cell analyzer comprising:
a sample preparation part configured for preparing a measurement sample from a blood sample and a reagent;
a measuring part configured for measuring blood cells in the measurement sample and obtaining measurement data of the blood cells;
a display;
a display controller configured for displaying a measurement registration screen on the display, wherein the measurement registration screen comprises:
an animal species selector for selecting one animal species from a plurality of animal species;
a minor classification selector for selecting one minor classification from a plurality of minor classifications, each of which represents a minor classification of the selected animal species;
a blood cell analysis mode selector for selecting one blood cell analysis mode from a plurality of blood cell analysis modes;
wherein the animal species selector, the minor classification selector and the blood cell analysis mode selector are displayed simultaneously;
an analytical condition storage part configured for storing a plurality of analytical conditions for determining whether or not measurement data is abnormal, wherein the analytical conditions correspond to each of said minor classifications and each of said blood cell analysis modes; and
an analysis controller configured for counting a number of blood cells by analyzing the measurement data according to one of the plurality of analytical conditions corresponding to the selected minor classification and the selected blood cell analysis mode.

2. The blood cell analyzer according to claim 1, further comprising:
a classification storage part configured for storing said selected animal species and said selected minor classification corresponding to said selected animal species in association with each other,
wherein said display controller displays said measurement registration screen displaying said selected minor classification corresponding to said selected animal species selected by said animal species selector in said classification storage part on the display.

3. The blood cell analyzer according to claim 1, wherein said analysis controller determines whether or not said number of blood cells is normal by comparing said number of blood cells with a threshold.

4. The blood cell analyzer according to claim 1, wherein each of said analytical conditions includes a determination formula for determining whether or not it is necessary to output a predetermined message as to said number of blood cells, and
wherein said analysis controller determines whether or not it is necessary to output a predetermined message as to said number of blood cells using said number of blood cells and said determination formula.

5. The blood cell analyzer according to claim 1, wherein said display controller displays said measurement registration screen including a list of minor classifications corresponding to said selected animal species selected by said animal species selector when said animal species is selected, and
wherein said display controller displays said measurement registration screen including only said selected minor classification when said selected minor classification is selected by said minor classification selector.

6. The blood cell analyzer according to claim 1, further comprising:
a classification storage part configured for storing said selected minor classification and attribute information of said selected minor classification in association with each other, and
an attribute information display part for reading said attribute information corresponding to said selected minor classification from said classification storage part and for displaying said read attribute information on said display when said minor classification selector selects said selected minor classification.

7. The blood cell analyzer according to claim 1, wherein said selected minor classification includes a category prepared by subdividing said selected animal species using a state of the animal.

8. The blood cell analyzer according to claim 1, further comprising a minor classification registration part for accepting registration of said selected minor classification,
wherein said display controller displays the measurement registration screen including said selected minor classification corresponding to said selected animal species in said selected minor classification accepted by said minor classification registration part.

9. The blood cell analyzer according to claim 1, wherein the blood cell analysis modes comprise:
a first blood cell analysis mode for counting red blood cells, white blood cells and platelets; and
a second blood cell analysis mode for counting red blood cells, white blood cells and platelets and for analyzing lymphocytes, monocytes, eosinophiles, neutrophiles and basophiles.

10. The blood cell analyzer according to claim 9, wherein the blood cell analysis modes comprise a third blood cell analysis mode for counting red blood cells, white blood cells and platelets and for analyzing lymphocytes, monocytes, eosinophiles, neutrophiles, basophiles and reticulocytes.

11. The blood cell analyzer according to claim 10, wherein the blood cell analysis modes comprise a fourth blood cell analysis mode for counting red blood cells, white blood cells and platelets and analyzing reticulocytes.

* * * * *